US009474903B2

(12) United States Patent
Chen et al.

(10) Patent No.: US 9,474,903 B2
(45) Date of Patent: Oct. 25, 2016

(54) CLINICAL RESPONSE DATA MAPPING

(71) Applicant: BOSTON SCIENTIFIC NEUROMODULATION CORPORATION, Valencia, CA (US)

(72) Inventors: Dean Chen, Los Angeles, CA (US); Brian James Hoffer, San Francisco, CA (US); Sridhar Kothandaraman, Valencia, CA (US); David Ari Lubensky, San Francisco, CA (US); Mun Pook Lui, Northridge, CA (US); Michael A. Moffitt, Valencia, CA (US); Dennis Allen Vansickle, Lancaster, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 123 days.

(21) Appl. No.: 14/212,730

(22) Filed: Mar. 14, 2014

(65) Prior Publication Data

US 2014/0277284 A1  Sep. 18, 2014

Related U.S. Application Data

(60) Provisional application No. 61/793,773, filed on Mar. 15, 2013, provisional application No. 61/830,855, filed on Jun. 4, 2013.

(51) Int. Cl.
*A61N 1/36* (2006.01)
*A61N 1/372* (2006.01)

(52) U.S. Cl.
CPC ....... *A61N 1/36132* (2013.01); *A61N 1/37235* (2013.01); *A61N 1/37241* (2013.01); *A61N 1/37247* (2013.01)

(58) Field of Classification Search
CPC ................. G06F 19/3406; A61N 1/37247
See application file for complete search history.

(56) References Cited

U.S. PATENT DOCUMENTS 5,099,846 A   3/1992  Hardy
5,361,763 A   11/1994 Kao et al.
(Continued)

FOREIGN PATENT DOCUMENTS

WO       01/90876 A1    11/2001
WO    2004/019799 A2     3/2004
(Continued)

OTHER PUBLICATIONS

European Patent Office, International Search Report and the Written Opinion/ ISA in International Application No. PCT/US2014/028264, mailed Nov. 11, 2014, 20 pages.
(Continued)

*Primary Examiner* — Michael Kahelin
(74) *Attorney, Agent, or Firm* — Lowe Graham Jones PLLC; Bruce E. Black

(57) ABSTRACT

A system and method include a processor that, based on at least a subset of stored data of clinical effects of one or more stimulations of anatomical tissue performed using electrodes of an implanted leadwire, generates and outputs at least one graphical marking representing the at least the subset of the stored data. Each of the at least one graphical marking represents a respective portion of the at least the subset of the stored data and is output in association with a respective set of values for each of at least two parameters by which one or more the stimulations were performed. The markings are plotted in a graph defined by axes corresponding to values of respective stimulation parameters. Alternative, the markings are arranged in a column of a tabular report. The markings are two-toned to provide respective information for both therapeutic and adverse side effects.

42 Claims, 6 Drawing Sheets

(56) References Cited

U.S. PATENT DOCUMENTS

| | | |
|---|---|---|
| 5,452,407 A | 9/1995 | Crook |
| 5,724,985 A | 3/1998 | Snell et al. |
| 5,782,762 A | 7/1998 | Vining |
| 5,938,688 A | 8/1999 | Schiff |
| 6,066,163 A | 5/2000 | John |
| 6,083,162 A | 7/2000 | Vining |
| 6,106,460 A | 8/2000 | Panescu et al. |
| 6,240,308 B1 | 5/2001 | Hardy et al. |
| 6,289,239 B1 | 9/2001 | Panescu et al. |
| 6,310,619 B1 | 10/2001 | Rice |
| 6,319,241 B1 | 11/2001 | King et al. |
| 6,351,675 B1 | 2/2002 | Tholen et al. |
| 6,389,311 B1 | 5/2002 | Whayne et al. |
| 6,463,328 B1 | 10/2002 | John |
| 6,491,699 B1 | 12/2002 | Henderson et al. |
| 6,539,263 B1 | 3/2003 | Schiff et al. |
| 6,622,048 B1 | 9/2003 | Mann et al. |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,003,352 B1 | 2/2006 | Whitehurst |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,209,787 B2 | 4/2007 | DiLorenzo |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,242,984 B2 | 7/2007 | DiLorenzo |
| 7,252,090 B2 | 8/2007 | Goetz |
| 7,254,446 B1 | 8/2007 | Erickson et al. |
| 7,257,447 B2 | 8/2007 | Cates et al. |
| 7,266,412 B2 | 9/2007 | Stypulkowski |
| 7,295,876 B1 | 11/2007 | Erickson |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 7,826,902 B2 | 11/2010 | Stone et al. |
| 7,848,802 B2 | 12/2010 | Goetz et al. |
| 8,180,601 B2 | 5/2012 | Butson et al. |
| 8,452,415 B2 | 5/2013 | Goetz et al. |
| 2004/0034394 A1 | 2/2004 | Woods et al. |
| 2004/0044279 A1 | 3/2004 | Lewin et al. |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0171587 A1 | 8/2005 | Daglow et al. |
| 2005/0228250 A1 | 10/2005 | Bitter et al. |
| 2006/0017749 A1 | 1/2006 | McIntyre et al. |
| 2006/0020292 A1 | 1/2006 | Goetz et al. |
| 2006/0094951 A1 | 5/2006 | Dean et al. |
| 2006/0235472 A1 | 10/2006 | Goetz et al. |
| 2006/0259079 A1 | 11/2006 | King |
| 2007/0017749 A1 | 1/2007 | Dold et al. |
| 2007/0043268 A1 | 2/2007 | Russell |
| 2007/0049817 A1 | 3/2007 | Preiss et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0191912 A1 | 8/2007 | Fischer et al. |
| 2007/0197891 A1 | 8/2007 | Shachar et al. |
| 2007/0203450 A1 | 8/2007 | Berry |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0071150 A1 | 3/2008 | Miesel et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0123923 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0269588 A1 | 10/2008 | Csavoy et al. |
| 2008/0300654 A1 | 12/2008 | Lambert et al. |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0204192 A1 | 8/2009 | Carlton et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0023130 A1 | 1/2010 | Henry et al. |
| 2010/0049276 A1 | 2/2010 | Blum et al. |
| 2010/0049280 A1 | 2/2010 | Goetz |

(56) References Cited

U.S. PATENT DOCUMENTS

| | | |
|---|---|---|
| 2011/0191275 A1 | 8/2011 | Lujan et al. |
| 2012/0302912 A1 | 11/2012 | Moffitt et al. |
| 2012/0316619 A1 | 12/2012 | Goetz et al. |

FOREIGN PATENT DOCUMENTS

| | | |
|---|---|---|
| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |
| WO | 2010/120823 A2 | 10/2010 |
| WO | 2011/139779 A1 | 11/2011 |
| WO | 2011/159688 A2 | 12/2011 |

OTHER PUBLICATIONS

Butson et al., "Current Steering to Control the Volume of Tissue Activated During Deep Brain Stimulation," Brain Stimulation 1, 2008, pp. 7-15.

Butson et al., "Patient Specific Analysis of the volume of tissue activated during deep brain stimulation," NeuroImage, Academic Press, vol. 34, No. 2, Dec. 2, 2006, pp. 661-670.

Butson et al., "Role of Electrode Design on the Volume of Tissue Activated During Deep Brain Stimulation," Journal of Neural Engineering, Mar. 1, 2006, vol. 3, No. 1, pp. 1-8.

Butson et al., "StimExplorer: Deep Brain Stimulation Parameter Selection Software System," Acta Neurochirugica, Jan. 1, 2007, vol. 97, No. 2, pp. 569-574.

Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al., "Sketching and Composing Widgets for 3D Manipulation," Eurographics, Apr. 2008, vol. 27, No. 2, pp. 301-310.

Izad, Olivier, "Computationally Efficient Method in Predicating Axonal Excitation," Dissertation for Masters Degree, Department of Biomedical Engineering, Case Western Reserve University, May 2009, 144 pages.

Jaccard, Paul, "Étude comparative de la distribution florale dans une portion odes Aples et des Jura," Bulletin de la Société Vaudoise des Sciences Naturelles (1901), vol. 37, pp. 547-579.

Dice, Lee R., "Measures of the Amount of Ecologic Association Between Species," Ecology 26(3) (1945), pp. 297-302. doi:10.2307/1932409, http://jstor.org/stable/1932409.

Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.

Hubert, Lawrence et al., "Comparing partitions," Journal of Classification 2(1) (1985), pp. 193-218, doi:10.1007/BF01908075.

Cover, T.M. et al., "Elements of information theory," (1991) John Wiley & Sons, New York, NY, pp. 1-542.

Meila, Marina, "Comparing Clusterings by the Variation of Information," Learning Theory and Kernel Machines (2003), pp. 173-187.

European Patent Office, International Search Report in International Application No. PCT/US2012/053344, dated Nov. 26, 2012, 8 pages.

European Patent Office, International Search Report in International Application No. PCT/US2012/050181, dated Jan. 3, 2013, 7 pages.

Euopean Patent Office, International Search Report and the Written Opinion in International Application No. PCT/US2012/050170, dated Oct. 5, 2012, 15 pages.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al, "Fast and robust multi-atlas segmentation of brain magnetic resonance images," NeuroImage, Academic Press, vol. 49, No. 3, Feb. 1, 2010, pp. 2352-2365.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

European Patent Office, International Search Report in International Application No. PCT/US09/03017, dated Aug. 3, 2009, 7 pages.

European Patent Office, International Search Report in International Application No. PCT/US09/03038, dated Oct. 8, 2009, 9 pages.

European Patent Office, International Search Report in International Application No. PCT/US09/03040, dated Aug. 13, 2009, 7 pages.

European Patent Office, International Search Report in International Application No. PCT/US09/03049, dated Jan. 26, 2010, 8 pages.

European Patent Office, partial International Search Report in International Application No. PCT/US2012/030701, dated Feb. 15, 2013, 7 pages.

European Patent Office, partial International Search Report in International Application No. PCT/US2012/030705, dated Mar. 6, 2013, 7 pages.

European Patent Office, International Search Report and Written Opinion in International Application No. PCT/US2012/030700, dated Feb. 27, 2013, 9 pages.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

European Patent Office, International Search report and Written Opinion in PCT application No. PCT/US12/050174, dated Mar. 6, 2013, 20 pages.

European Patent Office, International Search Report and Written Opinion in International Application No. PCT/US2012/050187, dated Feb. 27, 2013, 9 pages.

European Patent Office, International Search Report in International Application No. PCT/US09/03041, dated Aug. 20, 2009, 7 pages.

European Patent Office, International Search Report and the Written Opinion of the International Searching Authority in International Application No. PCT/US2012/050175, dated Oct. 26, 2012, 15 pages.

FIG. 5

CLINICAL RESPONSE DATA MAPPING

CROSS-REFERENCE TO RELATED APPLICATIONS

The present application claims the benefit of U.S. Prov. Pat. App. Ser. No. 61/793,773 ("the '773 application"), filed Mar. 15, 2013. The present application also claims the benefit of U.S. Prov. Pat. App. Ser. No. 61/830,855 ("the '855 application"), filed Jun. 4, 2013.

The present application is related to subject matter of U.S. Prov. Pat. App. Ser. Nos. 61/491,092 ("the '092 application") filed May 27, 2011, 61/693,866 ("the '866 application") filed Aug. 28, 2012, 61/699,115 ("the '115 application") filed Sep. 10, 2012, 61/699,135 ("the '135 application") filed Sep. 10, 2012, and 61/753,232 ("the '232 application") filed Jan. 16, 2013.

The present application is also related to U.S. patent application Ser. No. 13/481,524 ("the '524 application") and Ser. No. 13/481,497 ("the '497 application"), both of which were filed May 25, 2012 and claim priority to the '092 application.

The contents of all of the '773, '855, '092, '866, '115, '135, '232, '524, and '497 applications are incorporated by reference herein in their entireties.

FIELD OF THE INVENTION

The present invention relates to a system and method for generating and outputting a clinical response data map in which recorded clinical response data are graphically represented in correlation with stimulation program settings for a leadwire, e.g., of a Deep Brain Stimulation (DBS) device, a Spinal Cord Stimulation (SCS) device, or other stimulation device. Features of the present invention can aid the selection of electrical stimulation parameters for performing anatomic stimulation using the leadwire.

BACKGROUND

Stimulation of anatomical regions of a patient is a clinical technique for the treatment of disorders. Such stimulation can include deep brain stimulation (DBS), spinal cord stimulation (SCS), Occipital NS therapy, Trigemenal NS therapy, Vagus NS therapy, peripheral field stimulation therapy, sacral root stimulation therapy, or other such therapies. For example, DBS can include stimulation of the thalamus or basal ganglia and may be used to treat disorders such as essential tremor, Parkinson's disease (PD), and other physiological disorders, including psychiatric disorders. DBS can also be useful for traumatic brain injury and stroke. DBS is also used for treating dystonia, epilepsy, and obsessive-compulsive disorder.

However, understanding of the therapeutic mechanisms of action remains elusive. The stimulation parameters, electrode geometries, or electrode locations that are best suited for existing or future uses of DBS also are unclear.

For conducting a therapeutic stimulation, a neurosurgeon can select a target region within the patient anatomy, e.g., within the brain for DBS, an entry point, e.g., on the patient's skull, and a desired trajectory between the entry point and the target region. The entry point and trajectory are typically carefully selected to avoid intersecting or otherwise damaging certain nearby critical structures or vasculature. A stimulation electrode leadwire used to provide the stimulation to the relevant anatomical region is inserted along the trajectory from the entry point toward the target region. The stimulation electrode leadwire typically includes multiple closely-spaced electrically independent stimulation electrode contacts.

The target anatomical region can include tissue that exhibit high electrical conductivity. For a given stimulation parameter setting, a respective subset of the fibers are responsively activated. A stimulation parameter can include a current amplitude or voltage amplitude, which can be the same for all of the electrodes of the leadwire, or which can vary between different electrodes of the leadwire. The applied amplitude setting results in a corresponding current in the surrounding fibers, and therefore a corresponding voltage distribution in the surrounding tissue. The complexity of the inhomogeneous and anisotropic fibers makes it difficult to predict the particular volume of tissue influenced by the applied stimulation.

A treating physician typically would like to tailor the stimulation parameters (such as which one or more of the stimulating electrode contacts to use, the stimulation pulse amplitude, e.g., current or voltage depending on the stimulator being used, the stimulation pulse width, and/or the stimulation frequency) for a particular patient to improve the effectiveness of the therapy. Parameter selections for the stimulation can be achieved via tedious and variable trial-and-error, without visual aids of the electrode location in the tissue medium or computational models of the volume of tissue influenced by the stimulation. Such a method of parameter selection is difficult and time-consuming and, therefore, expensive. Moreover, it may not necessarily result in the best possible therapy.

Systems have been proposed that provide an interface that facilitates parameter selections. See, for example, U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), and U.S. patent application Ser. No. 12/454,314, filed May 15, 2009 ("the '314 application"), the content of each of which is hereby incorporated herein by reference in its entirety.

The leadwire can include cylindrically symmetrical electrodes, which, when operational, produce approximately the same electric values in all positions at a similar distance from the electrode in any plane that cuts through the electrode. Alternatively, the leadwire can include directional electrodes that produce different electrical values depending on the direction from the electrode. For example, the leadwire can include multiple separately controllable electrodes arranged cylindrically about the leadwire at each of a plurality of levels of the leadwire. Each electrode may be set as an anode or cathode in a bipolar configuration or as a cathode, with, for example, the stimulator casing being used as ground, in a monopolar arrangement.

When programming a leadwire for tissue stimulation, e.g., DBS, the clinical standard of care is often to perform a monopolar review (MPR) upon activation of the leadwire in order to determine the efficacy and side-effect thresholds for all electrodes on the leadwire, on an electrode-by-electrode basis. Monopolar review, rather than bipolar review, is performed because monopolar stimulation often requires a lower stimulation intensity than bipolar stimulation to achieve the same clinical benefit. The MPR can inform the selection of a first clinical program (parameters for stimulation) for treating a patient.

Example systems for programming a leadwire for tissue stimulation display a graphical representation of an area within which it is estimated that there is or could be tissue activation, referred to herein as a volume of activation (VOA), that results from input stimulation parameters. For example, the VOA can be calculated as a region outside of which stimulation is estimated to be unlikely. The VOA can be displayed relative to an image or model of a portion of the patient's anatomy.

Generation of the VOA may be based on Neural Element Models such as a model of fibers, e.g., axons, and a voltage distribution about the leadwire and on detailed processing thereof. Performing such processing to provide a VOA preview in real-time response to a clinician's input of parameters is not practical because of the significant required processing time. Therefore, conventional systems pre-process various stimulation parameter settings to determine which axons are activated by the respective settings.

Those systems also provide interfaces via which to input selections of the stimulation parameters and notes concerning therapeutic and/or side effects of stimulations associated with graphically represented VOAs. The systems also allow user input of, or automatically determine, a target stimulation region, e.g., within or encompassing one or more defined anatomic structures, or allow user input of, or automatically determine, a target defined anatomic structure, which target region or structure is targeted for stimulation.

SUMMARY

Example embodiments of the present invention provide a system and method for providing a therapy effect history map. Example embodiments of the present invention provide a system and method for inputting therapy effect information in relation to a therapy effect map. Example embodiments of the present invention provide a system and method for selecting therapy parameters using an interface that includes a map, which map includes a plurality of positions corresponding to respective therapy parameters which may be selected by the user. According to an example embodiment, the map is also a therapy effect map.

Thus, according to an example embodiment, the therapy effect history map is integrated with a system for parameter selection, which selected parameters are, according to an example embodiment, usable for programming an implanted leadwire, using the same interface and/or system in which the therapy effect history map is provided. According to an alternative example embodiment, the therapy effect history map is provided as a stand-alone program and/or system, separate from the application used for programming the leadwire.

According to an example embodiment of the present invention, a system is configured to obtain information representing one or more effects of a stimulation therapy. According to an example embodiment, the system is configured to receive information concerning therapeutic and/or adverse side effects of a stimulation therapy. In an example embodiment, the information is received in connection with particular stimulation parameters and the system stores the effects information in association with the stimulation parameters to which the information indicates the effects relate.

In an example embodiment of the present invention, the system generates, and outputs in a user interface, a map whose positions correspond to different respective stimulation parameter sets with respect to, for example, two (or more) predefined or user-selected parameters. For example, according to an example embodiment, the map is a two-dimensional map, of which a first axis corresponds to position along a leadwire, e.g., a particular actual or virtual electrode, and a second axis corresponds to stimulation amplitude. (In an example embodiment, a virtual electrode is a leadwire position with which a stimulation is associated, as though the stimulation was produced by an electrode at that location, when, instead, the stimulation is actually produced by activation of a combination of a plurality of electrodes at other locations.)

According to the example embodiment in which one of the axis of the map corresponds to electrode position, the system outputs a, for example, two dimensional model of the leadwire as or alongside an edge of the map to represent or complements the values of the corresponding axis. In an example embodiment, the model includes representations of electrodes of the leadwire.

According to an example embodiment, populates the map with the received therapy effects information, different items of the information, associated with different combinations of the parameters to which the map positions correspond, being used for populating the different positions of the map.

According to an example embodiment of the present invention, the system generates a graphical marking including one or more variable visual characteristics, where the selected value(s) of the characteristic(s) indicates a respective aspect of the information associated with the map position which the graphical marking populates. A non-exhaustive list of example characteristics includes color, hatching, transparency, size, thickness, and shape.

According to an example embodiment of the present invention, where the information includes more than one recorded set of effects information for a single particular map position, the system generates one or more revised values for the effects based on a combination of the effects information recorded in association with the parameters to which the map position corresponds. For example, in an example embodiment, each of one or more of the records includes one or more respective scores, with the system calculating a score based on a combination, e.g., average, of the scores of the different records. For example, in an example embodiment, in an instance where a first record of effects of a stimulation conducted using a particular combination of electrode and amplitude indicates a side effect score of 1, representing a side effect of low severity, and a second record of effects of a stimulation using that same combination of electrode and amplitude indicates a side effect score of 4, representing a side effect of extreme severity, the system calculates a new score, e.g., the average score of 2.5, and populates the map position corresponding the electrode and amplitude combination with a graphical marking representative of the calculated combinatory score. According to an alternative example embodiment, the system uses the latest recorded effects information for a particular stimulation parameter set to which a map position corresponds for populating the map position.

According to an example embodiment, the obtained records associated with the parameters corresponding to a single map location can correspond to a plurality of patients who have been subjected to a stimulation at that parameter set; a plurality of indications, symptoms, and/or diseases for which different stimulations have been conducted for one or more patients; and/or a plurality of stimulation sessions conducted at different times for one or more patients. According to an example embodiment, the system provides a user interface component via which to receive user input of criteria by which to limit the scope of the stimulations whose information are used for populating the map. For example, the user can limit the population to information corresponding to stimulations associated with particular patients, e.g., a current patient being treated or patients having certain characteristics (e.g., those of a certain height, weight, gender, taking certain medications, etc.), particular diseases, particular times, e.g., the last 5 months, and/or particular sessions, e.g., last 5 sessions. These are just some of the usable filter parameters, and, according example embodiments, other filter parameters can be used. According to an example embodiment, a combination of filter parameters can be used. According to an example embodiment, subsequent to an initial display of the graphical markings using no or few filter parameters, the user can add filter parameters to gradually remove some of the markings. This can be useful because the user may want to see how various criteria impact stimulation score.

According to an example embodiment of the present invention, the graphical marking includes a plurality of parts, each corresponding to a different aspect of the information associated with the stimulation settings to which the map position populated by the graphical marking corresponds. For example, in an example embodiment received information includes an adverse side effect score and a therapeutic effect score, and the graphical marking includes a first part representative of the side effect score and a second part representative of the therapeutic effect score. Still further, according to an example embodiment, different scores may be obtained, and accordingly represented by respective parts of the graphical marking, for different adverse side effects, e.g., parasthesia, dyskenisia, etc., and different therapeutic effects, e.g., positive effects with respect to rigidity, tremor, etc. Still further, according to an example embodiment, the system calculates and represents as a respective part of the marking an overall score based on a combination of both adverse side effect information and therapeutic effect information, the adverse side effect score adversely affecting the overall score and the therapeutic effect score positively affecting the overall score.

For example, according to an example embodiment, the different parts of the graphical marking are concentrically arranged, one within the other, with different bands about the center dedicated for representing different types of information. That records corresponding to a particular map location include information regarding only one of the types to which the bands correspond can occur. According to an example embodiment, in such an instance, the band(s) corresponding to the missing information is left devoid of any of the graphical characteristics used for representing the information. For example, a pure black and solid band can be used where there is no information to represent for the particular band. The concentrically arranged marking can be a circle, square, or any other shape.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination, and to generate any of the user interface displays described herein, alone or in combination. The one or more processors can be embodied in a server or user terminal or combination thereof. The user terminal can be embodied, for example, as a desktop, laptop, hand-held device, Personal Digital Assistant (PDA), television set-top Internet appliance, mobile telephone, smart phone, iPad etc., or as a combination of one or more thereof. In an example embodiment, described features can be integrated with and be embodiment as a clinician programmer terminal, e.g., as referred to in the '330, '312, '340, '343, and '314 applications. Additionally, some of the described methods can be performed by a processor on one device or terminal and using a first memory, while other methods can be performed by a processor on another device and using, for example, a different memory. The features can be embodied in an application for a smartphone and/or iPad, for example.

The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to one or more hardware computer-readable media, e.g., as described above, on which are stored instructions executable by a processor to perform the methods and/or provide the user interface features described herein.

An example embodiment of the present invention is directed to a method, e.g., of a hardware component or machine, of transmitting instructions executable by a processor to perform the methods and/or provide the user interface features described herein.

Additionally, according to an example embodiment, system features draw upon data, such as clinical effects data for producing the therapy effect history map, and/or produce such data, where such data is obtained from and/or stored to a data store. The data store can be located, for example, on a simulator device, a computer used for inputting such data, a patient remote control usable by the patient for adjusting stimulation parameters of an implanted stimulation leadwire, a central local database, or a cloud database. According to an example embodiment, the data store stores data of a plurality of patients, the data of the plurality of patients being used for generating a single therapy effect history map. According to an alternative or additional embodiment, the system generates a therapy effect history map for a particular patient selectively using only the clinical history data of only the respective patient.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIG. 5 shows a report including a column of graphical clinical effects representations generatable by a processor based on clinical effects data, according to an example embodiment of the present invention.

DETAILED DESCRIPTION

Figure 1:
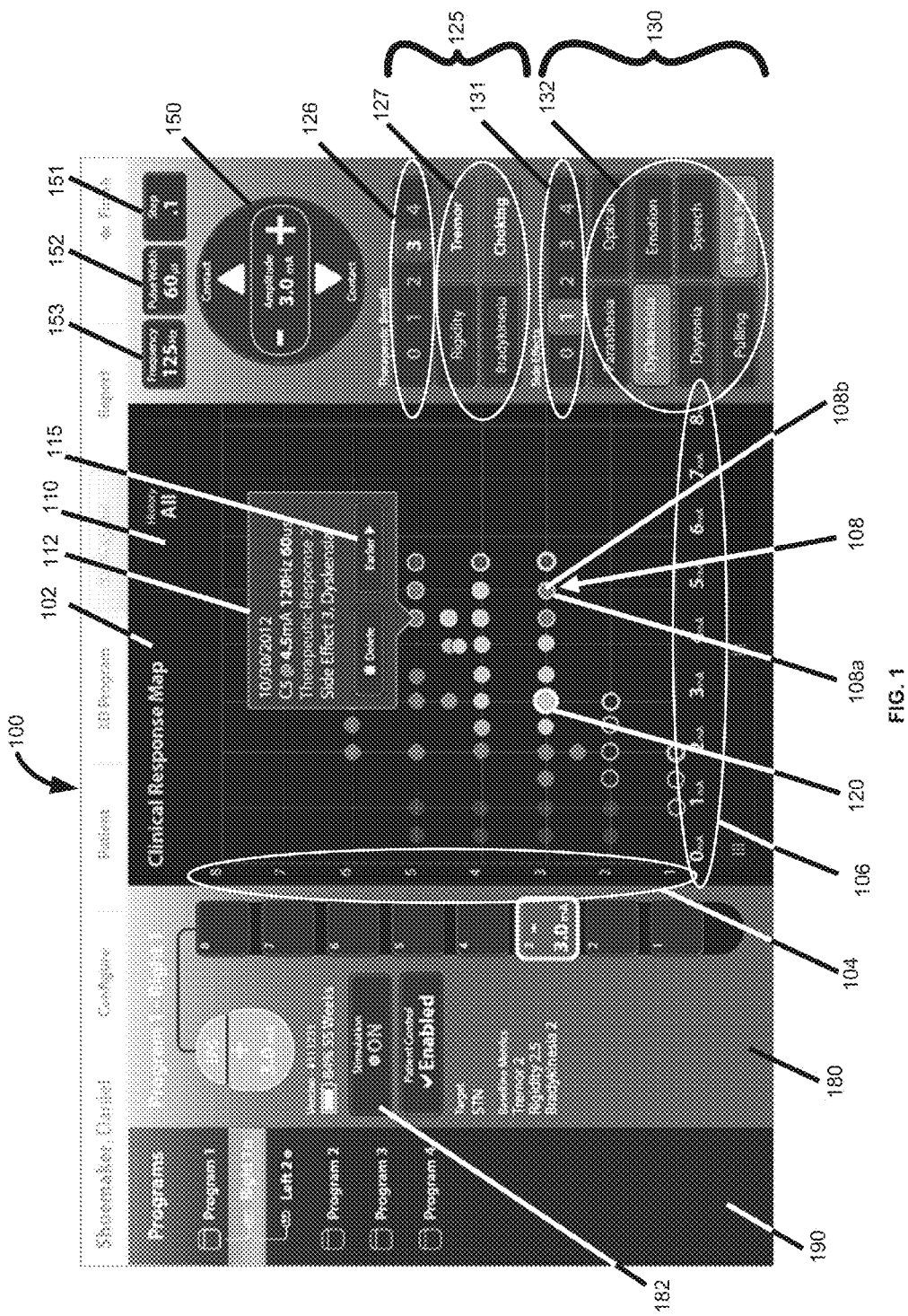
FIG. 1 is a screenshot of a graphical user interface including a clinical response map, according to an example embodiment of the present invention.

FIG. 1 shows an example user interface screen 100 generated and output according to an example embodiment of the present invention. The screen 100 includes a clinical response map 102 including a first axis 104 corresponding to leadwire position or electrode number and a second axis 106 corresponding to stimulation amplitude. Positions in the map therefore correspond to respective stimulations, each associated with activation of a respective actual or virtual electrode at a particular stimulation amplitude.

At those positions of the map corresponding to the electrode/amplitude combination for which the system has obtained clinical response information, e.g., in the form of an adverse side effect and/or therapeutic effect score, the system displays at respective ones of those positions respective graphical markings 108 (only one is labeled in FIG. 1 for purposes of clarity). The markings include a ring 108a about a center region 108b. For example, the ring 108a represents an adverse side effect score and the center region 108b corresponds to a therapeutic effect score.

According to an example embodiment, the ring 108a and the center region 108b are graphically demarcated from each other, for example by use of different colors and/or hatching. For example, according to an example embodiment, the center region 108b is filled (where a respective score is available) using a blue color and the ring 108a is filled (wherein a respective score is available) using a yellow color. For those map positions for which there is only an adverse side effect score, the appropriately colored ring 108a is displayed about an empty center region 108b, e.g., the center region 108b being black or whichever other background color is used for the map 102. Similarly, for those map positions for which there is only a therapeutic effect score, the appropriately colored center region 108b is displayed without any ring 108a surrounding the center region 108b or with only a ring outline where the ring 108a would otherwise be displayed, the ring outline being black filled, or filled with whichever other background color is used for the map 102.

In FIG. 1, the center regions 108b of different ones of the graphical markings 108 are differently saturated with the selected color, i.e., their transparencies differ, in correspondence with differences in their respective scores. For example, the center regions 108b of the graphical markings 108 at those map positions associated with high therapeutic effect scores are highly saturated with the therapeutic effect color (with low transparency), and the center regions 108b of the graphical markings 108 at those map positions associated with low therapeutic effect scores are less saturated with the therapeutic effect color (with higher transparency). The degrees of saturation and transparency are many for representing many different scores.

In FIG. 1, the rings 108a of different ones of the graphical markings 108 are of different thicknesses in correspondence with differences in their respective scores. For example, the ring 108a of the graphical markings 108 at those map positions associated with high adverse side effect scores are thick, and the rings 108a of the graphical markings 108 at those map positions associated with low adverse effect scores thinner. The degrees of thickness are many for representing many different scores.

The user interface screen 100 includes a user-selectable criteria selector control 110, which can be selected for input of filter criteria for filtering the records used for generating the map 102. For example, FIG. 1 shows that all records are being used. (This may be limited to certain default filter criteria in any case. For example, the system may be set to limit the used records to those associated to a patient currently being programmed.) According to an example embodiment, responsive to selection of the control 110, the system provides input fields in which a user can input filter criteria, such as those described above, for limiting the records being used for the generation of the map.

According to an example embodiment of the present invention, the displayed graphical markings 108 are selectable, in response to which selection, the system outputs, e.g., textual, details concerning the effects information represented by the displayed graphical marking 108. For example, the interface screen 100 shown in FIG. 1 includes a details box 112 textually identifying details concerning the stimulation effects information of a selected one of the graphical markings 108. Such details, as shown in FIG. 1, can include the respective score(s) for therapeutic and/or adverse side effects and/or identifications of particular recorded therapeutic effects and/or side effects.

For example, as described in U.S. Pat. App. Ser. No. 61/699,135 ("the '135 application"), filed Sep. 10, 2012, the entire contents of which is hereby incorporated by reference herein, a user can input specific therapeutic effects and/or adverse side effects produced by a stimulation using a particular set of stimulation parameters. For example, the user can input data representing that a stimulation provides a therapeutic effect for one or more of rigidity, tremor, choking, bradykinesia, and/or other symptoms, and/or provides an adverse side effect such as, for example, one or more of parasthesia, dyskenisia, dystonia, etc. The user can input an overall therapeutic score and/or an overall adverse side effect score. (In an example embodiment, separate scores can be input for specific therapeutic and/or adverse side effects.)

For example, the details box 112 shows that the selected map position (i.e., the stimulation parameters to which the selected map position corresponds) is associated with a recorded adverse side effect of dyskenisia, with an overall therapeutic effect score of 2, and an overall adverse side effect of 3.

According to an example embodiment, as shown in FIG. 1, the details box 112 further identifies some of the stimulation parameters for which the clinical response information has been received. For example, the details box 112 includes information regarding a single stimulation session. For example, the details box 112 in FIG. 1 shows clinical response information obtained for a stimulation session that was performed on Oct. 30, 2012, with a stimulation at an amplitude of 4.5 mA, frequency of 120 Hz, and pulse width of 60 μs.

According to an example embodiment, and as shown in FIG. 1, if a map location is associated with clinical response records for a plurality of stimulation sessions of a patient that were conducted over time, the system further provides a session navigation control 115 for selecting different sessions, where, in response to a navigation instruction, input by a user using the navigation control 115 for navigating to a different session, the details box 112 is updated to reflect the information corresponding to the session to which the user has navigated. For example, the details box 112 can include an "earlier" button and/or a "later" button, only the former being shown in FIG. 1, for changing the stimulation session whose details are displayed to either an earlier or later session than the one that is currently displayed. According to an example embodiment, the graphical marking 108 is generated based on the information of all of the sessions (meeting any predefined or user-selected filter criteria), but the details box 112 shows the information of only one of the sessions at a time. However, according to an example embodiment, as noted above, a criteria selector control 110 is selectable by which to limit the sessions on which basis the characteristics of the graphical marking 108 are determined One such filter is a history filter, by which the user can select a particular one or more sessions on which basis to generate the graphical marking 108, and therefore, the characteristics of the graphical marking 108 can reflect the information of the single session whose details are provided in the details box 112, even where information of other sessions and corresponding clinical response records are stored.

According to an example embodiment of the present invention, the system and method display the map 102 in a touch-screen display, and the selection of a displayed graphical marking 108 can be by touch of the graphical marking 108. Alternative or additionally, according to an example embodiment, an input device, such as predetermined keys of a keyboard, a joystick, or navigation pad is usable for moving between different points of the map 102, to select different ones of the graphical markings 108.

According to an example embodiment of the present invention, the system and method display a cursor 120 for highlighting the currently selected graphical marking 108.

According to an example embodiment of the present invention, the system and method provide for user input of new session data, including clinical response information, by interaction with the map 102 for updating the map 102. For example, the user can move the cursor 120 to location of the map 102, for example, a location not currently populated with a graphical marking 108, input stimulation parameter information for the session, such as frequency and pulse width, and further input therapeutic and/or side effects information, for example, by selecting one or more of the therapeutic effect buttons 125 and/or one or more of the adverse side effect buttons 130. According to an example embodiment, the buttons 125 and 130 include overall intensity indicator buttons 126 and 131 by which to input, respectively, a general level of therapeutic and/or adverse side effect. According to an alternative example embodiment, the intensity indicator buttons 126 and 131 can be used to input scores on a per effect basis to indicate a degree of the respective indicated effects. According to an example embodiment, the buttons 125 and 130 include specific effect type indicator buttons 127 and 132 by which to input, respectively, particular types of therapeutic and/or adverse side effects associated with a session.

Figure 2:
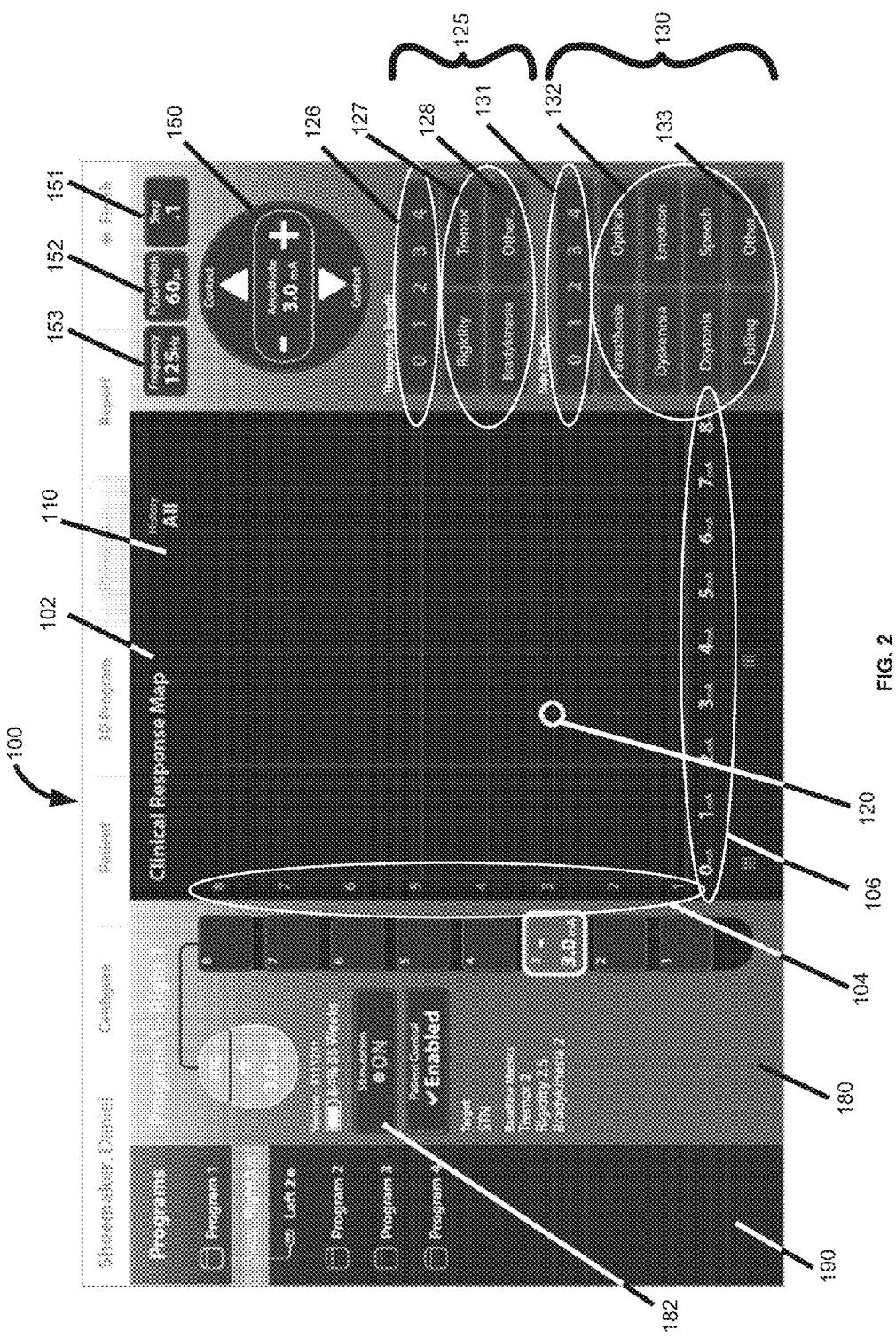
FIG. 2 is a screenshot of a graphical user interface including a clinical response map and including a control by which to bring up an extended menu of effect types, according to an example embodiment of the present invention.
Figure 3:
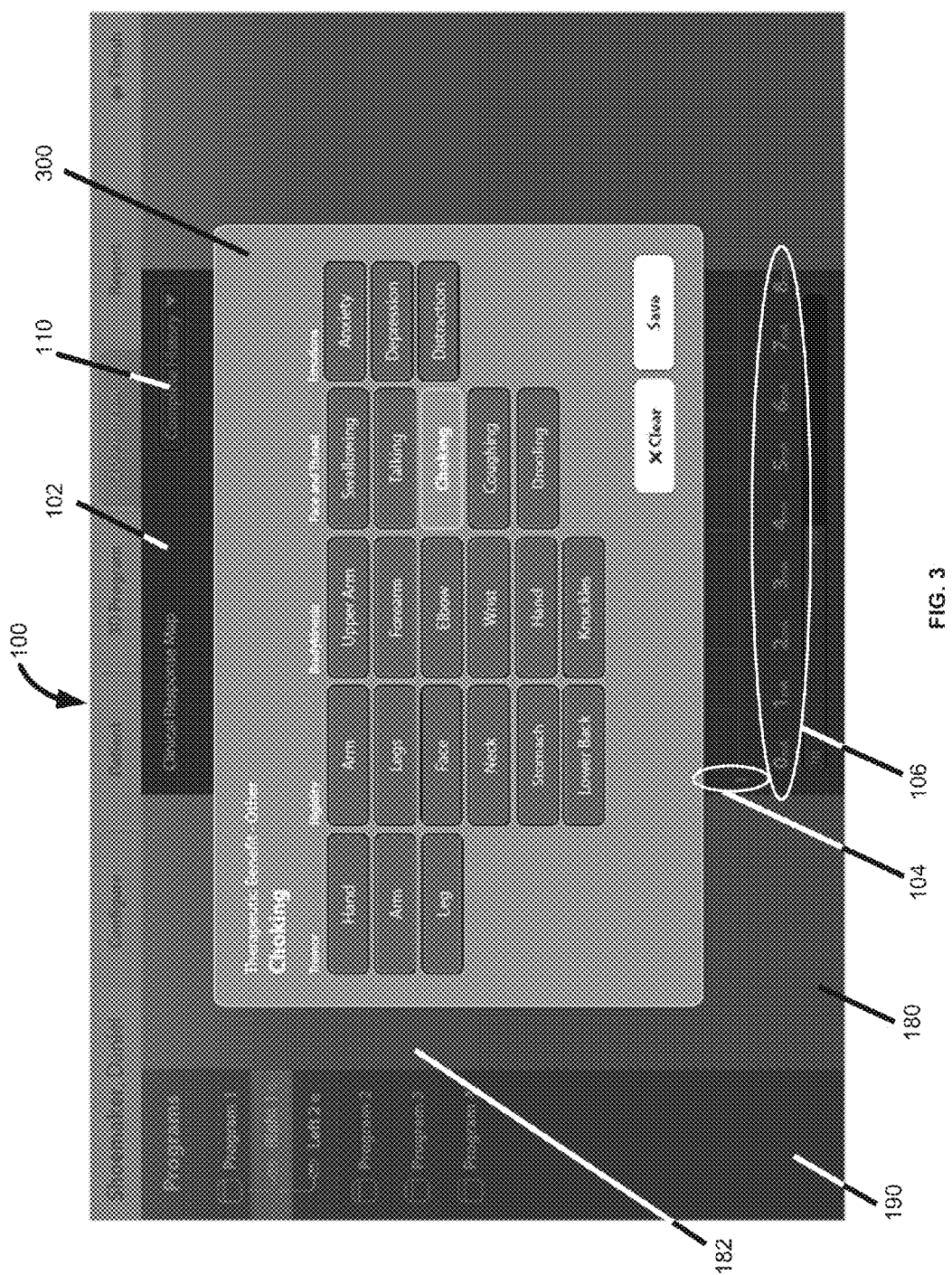
FIG. 3 is a screenshot showing an extended menu of effect types, according to an example embodiment of the present invention.

As shown in FIG. 2, according to an example embodiment, the clinical effect buttons 125 and 130 include respective "other" buttons 128 and 133 response to the selection of which the system and method display buttons corresponding to additional therapeutic effects and/or adverse side effects for which buttons are not displayed on the main screen. For example, FIG. 3 shows an example effect indicator menu screen 300 which includes additional buttons corresponding to respective therapeutic effects which the system and method display in response to selection of the "other" button 128, according to an example embodiment of the present invention.

According to an example embodiment, the map 102 is navigable between positions thereof. When a user navigates to a position of the map 102 at which a graphical marking 108 indicating clinical effect is displayed, the system highlights the one or more of the buttons 125 and 130 that were previously selected to indicate clinical effect, in accordance with which selection(s) the graphical marking 108 was generated. According to an example embodiment, if a map position at which a graphical marking 108 is displayed is associated with records of a plurality of stimulation sessions, the buttons that are highlighted are those selected for one of the sessions, e.g., whichever session is represented by the details box 112.

According to an example embodiment, information for a new session associated with electrode and amplitude settings corresponding to a position of the map 102 that is already populated with a graphical marking 108 can be input, based on which new input information, the graphical marking 108 can be updated. For example, according to an example embodiment, the system and method display a button by which a user can indicate that new session information is to be input. Alternatively or additionally, the system and method is configured to obtain other user input for entering a mode by which the user enters new session information. According to an example embodiment, a user can choose whether to update information of a stimulation session for which clinical effect information had previously been recorded or to input information for an entirely new session.

For example, although not shown, according to an example embodiment of the present invention, the details box 112 includes a button for updating a session whose details are displayed in the details box 112 and/or includes a button for input of new session information.

In addition, according to an example embodiment, and as shown in FIG. 1, the details box 112 includes a "delete" button for removing a clinical response record. For example, if the graphical marking 108 at a position is based on a single clinical response record that is being deleted, the graphical marking 108 is also responsively removed. If the graphical marking 108 is based on a number of stimulation response records, then the graphical marking 108 is updated to reflect removal of the effect thereon by the clinical response record being removed.

As shown in FIG. 1, a plurality of graphical markings 108 can overlap where clinical response information is recorded for settings that only slightly differ with respect to electrode location and/or amplitude setting.

According to an example embodiment of the present invention, the system and method provide a navigation pad for navigating between different positions of the map 102. For example, FIG. 1 shows a displayed user-interactive navigation pad 150 that includes a first section (shown in FIG. 1 to be represented by an up arrow) to shift the cursor 120 to a map position corresponding to a higher electrode position of the leadwire than to which the current map position of the cursor 120 corresponds; a second section (shown in FIG. 1 to be represented by a down arrow) to shift the cursor 120 to a map position corresponding to a lower electrode position of the leadwire than to which the current map position of the cursor 120 corresponds; a third section (shown in FIG. 1 to be represented by a '+' sign) to shift the cursor 120 to a map position corresponding to a higher amplitude level than to which the current map position of the cursor 120 corresponds; and a fourth section (shown in FIG. 1 to be represented by a '−' sign) to shift the cursor 120 to a map position corresponding to a lower amplitude level than to which the current map position of the cursor 120 corresponds. The pad 150 is a tool that provides the user with more control to fine tune the cursor position. According to an example embodiment, and as shown in FIG. 1, the system and method display in the navigation pad 150 a textual indication of the amplitude setting to which the current cursor location corresponds.

According to an example embodiment, and as shown in FIG. 1, the system and method provide, e.g., display, a step size control 151 by which the user can toggle between different step sizes, e.g., 0.1 and 0.5, by which each selection of the regions of the navigation pad 150 corresponding to amplitude effects the selected amplitude for repositioning of the cursor 120. For example, while the step size control 151 is set to the 0.1 step-size, each selection of the '+' sign of the pad 150 is interpreted as an instruction to move the cursor 120 to a position of the map that corresponds to an amplitude setting that is 0.1 higher than that to which the current cursor position corresponds, whereas, while the step size control 151 is set to the 0.5 step-size, each selection of the '+' sign of the pad 150 is interpreted as an instruction to move the cursor 120 to a position of the map that corresponds to an amplitude setting that is 0.5 higher than that to which the current cursor position corresponds. Similarly, selection of the '−' sign is interpreted as an instruction to move the cursor 120 to a position of the map that corresponds to an amplitude setting that is 0.1 or 0.5 (depending on the step size setting) lower than that to which the current cursor position corresponds.

According to an example embodiment, the cursor 120 can be dragged via a touch-screen. According to an alternative example embodiment, the user can touch any point in the map 102, responsive to which the system shifts the cursor 120 to the touched position of the map 102.

According to an example embodiment of the present invention, and as shown in FIG. 1, the system and method output, e.g., display, toggle buttons 152 and 153 by which to toggle between different common settings for other stimulation parameters, such as frequency and pulse width. While such other parameters do not affect map position of the cursor 120 (in an embodiment in which the map 102 is two dimensional with one axis corresponding to electrode location and the other axis corresponding to amplitude), nevertheless the indicated values for such other parameters are, according to an example embodiment, indicated in the details box 112. Moreover, according to an example embodiment of the present invention, the selected values for such other parameters are used as filter criteria to filter the data on whose basis the clinical response map 102 is generated. For example, if the user selects a pulse width of 60 μs and a frequency of 125 Hz, the system generates the graphical markings 108 based on only that data which corresponds to stimulations performed at those settings. According to an alternative example embodiment, the system does not use the parameters as filter criteria. According to an alternative example embodiment, the system is configured to obtain user input selecting whether to apply one or more of the settings as filter criteria for filtering the data on whose basis to generate the graphical markings 108. The selected parameter settings can similarly be used to filter the data used for generating other described aspects of the user interface, e.g., the records traversable using the session navigation control 115.

Figure 4:
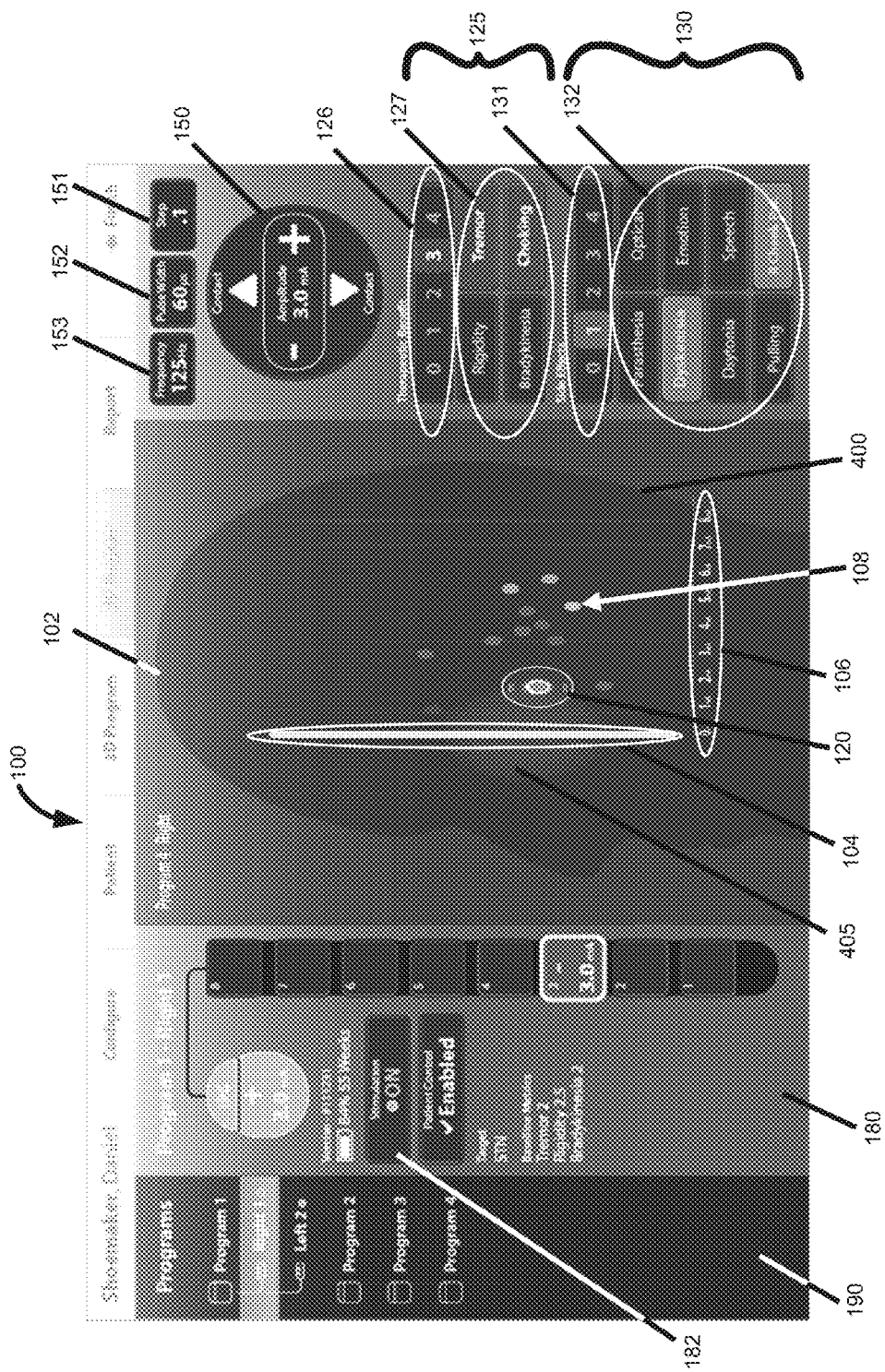
FIG. 4 is a screenshot showing a clinical response map overlapping a representation of an anatomical structure and including a circular indicator of stimulation magnitude, according to an example embodiment of the present invention.

According to an example embodiment, and as shown in FIG. 4, the system and method display the clinical response map 102 overlapping an anatomical region representation 400 that graphically represents an anatomical region in which the leadwire is implanted. For example, if the leadwire is implanted in the brain of a patient, then, according to an example embodiment, the anatomical region representation 400 is a silhouette of a head. Such an overlapping display can visually indicate how the electrodes location along the leadwire corresponds to the implant location.

According to an example embodiment of the present invention, and as shown in FIG. 4, the system and method display a circle 405, centered on the electrode location to which the map position at which the cursor 120 is positioned corresponds and the outer perimeter of which passes through the map position at which the cursor 120 is positioned to provide the user with an indication of a relative magnitude of stimulation reach for the amplitude to which the cursor position corresponds. According to an example embodiment of the present invention, although the different amplitude levels are evenly spaced apart according to value interval, the value spacing is selected so that the size of the circle 405 corresponding to amplitude value approximately indicates an actual expected reach of produced electric field or tissue activation.

According to an example embodiment, aside from using the map 102 to review previously recorded clinical response information and/or to enter new clinical response data, the map 102 is usable for setting leadwire parameters to program an implanted pulse generator (IPG), for causing the leadwire to stimulate an anatomical region of a patient. For example, according to an example embodiment, a user can navigate to a position in the map 102, which position corresponds to a particular electrode (actual or virtual) and amplitude setting, and can select a control interpreted by the system as an instruction to program the IPG accordingly. If frequency and pulse width values need to be changed, controls, for example as described above, can be used to modify the values of those parameters before input of the instruction to program the IPG.

For example, FIG. 1 shows the clinical response map 102 displayed in a same display screen as, and alongside, program panel 180 displaying information of a selected stimulation program. As the user navigates the clinical response map 102, the program information is responsively updated in the program panel 180. The program panel 180 includes a stimulation application toggle button 182 to toggle between turning the program on and off. When the user selects the stimulation toggle button 182 to turn the stimulation on, the system responsively programs the IPG with the stimulation parameters to which the selected position of the map 102 corresponds.

According to an alternative example embodiment, the system includes one control for toggling between turning a stimulation program on and off and another control for selecting whether to apply settings to which the map position corresponds to the program. For example, the IPG can be causing the leadwire to stimulate a tissue region according to the stimulation program which has been turned on. While the stimulation is ongoing, the user can use the map 102 to select new settings, and then select a button interpreted as an instruction to apply the new settings to the program currently being implemented.

According to an alternative example embodiment, the system and method provide a program mode and a clinical response entry and viewing mode. When in the program mode, the user's selection of a position within the map 102 is automatically interpreted as an instruction to program the IPG according to the parameters to which the selected map position corresponds, but, when in the clinical response entry and viewing mode, the selection of a position in the map 102 provides for viewing and/or inputting clinical response information as described above. According to an example embodiment, even in the program mode, the system and method display the graphical markings 108, and, in an example embodiment, show the details box 112 and highlight previously selected ones of the buttons 125 and/or 130 where such information is available for the selected position of the map 102.

According to an alternative example embodiment, a map position is selectable in more than one way. If a first selection method is used, the details box 112 is displayed and if a second selection method is used, the program is set with the corresponding parameters. For example, cursor movement by drag or selection of a cursor movement input control can be used for changing program settings, and touch of a position can be used for viewing and/or updating clinical response information. Alternatively, the different selection methods can be left-click and right-click.

More than one leadwire may be implanted in a patient. Additionally, a clinician may set up a number of programs to be implemented, for example, in a defined repetitive sequence, or at different predefined times or periods. Therefore, according to an example embodiment of the present invention, and as an example is shown in FIG. 1, the system and method display a program selection panel 190 in which a plurality of defined programs are listed, where the program listings are selectable. In an example embodiment in which two leadwires are implanted, in response to selection of a program listing, the system and method responsively expands the program listing to display selectable listings of the left and right implanted leadwires. The program panel 180 is populated with information for the selected leadwire of the selected program. For example, according to an example embodiment, the map 102 can be used for selecting parameter values with which to set the right leadwire for program 1, and can be used for likewise selecting parameter values with which to set the left leadwire for program 1, and/or the right and/or left leadwires for other programs.

According to an example embodiment, the system and method display, for example in the program panel 180, baseline metrics concerning symptoms targeted to be treated by the stimulations. According to an example embodiment, changes to such symptoms can be recorded over time in association with stimulation sessions, and the details box 112 shows the symptoms information recorded in association with the session whose details are displayed in the details box 112, to provide for easy comparison to the baseline symptoms.

According to an example embodiment, besides for the individual graphical markings 108 displayed at respective positions of the map 102, each marking representing clinical response data input for one or more sessions associated with stimulation using the electrode to which the map position corresponds at the amplitude level to which the map position corresponds, the system and method also displays a in the map 102 an umbrella graphical marking that spans many of the positions of the map 102, where a characteristic, e.g., color or color intensity, of the umbrella graphical marking gradually changes between positions of the map 102 based on the different clinical response data associated with different positions within the map 102. For example, according to an example embodiment, the system and method interpolates the clinical response data associated with different positions of the map 102 to obtain interpolated data for those positions not associated with clinical response data, thereby filling in the voids.

According to an example embodiment, the system and method display the umbrella graphical marking simultaneously with the graphical markings 108, and graphically demarcate the graphical markings 108 from the umbrella graphical marking. For example, according to an example embodiment, the graphical markings are outlined, e.g., with a black line, so that they stand out. Alternatively, the umbrella graphical marking is displayed using lighter shades of color than those used for the graphical markings 108, so that if, for example, a position of the map 102 is not associated with input clinical response data, but is assigned an interpolated clinical response value, the shade of color used at that position is softer than that used for a graphical marking 108 representing the same clinical response value.

According to an example embodiment, the system and method displays a first umbrella graphical marking representing the therapeutic effect data and a second umbrella graphical marking representing the adverse side effect data. Since they may be difficult to distinguish when they overlap each other, according to an example embodiment, the system and method provide a control by which the user can select which of the umbrella graphical markings to display, so that the user can thereby choose to display only one of them at a time.

According to an example embodiment, for each of the positions of the map 102 corresponding to recorded therapeutic and adverse side effect data, the system and method calculate an overall score based on both the therapeutic effect and adverse side effect information associated with the respective position, further calculate interpolated scores for the positions not associated with clinical response data, and output a single umbrella graphical marking based on the interpolated combinatory scores, which single umbrella marking gradually changes between positions according to the different scores, as described above. According to an example embodiment, the system and method first generate interpolated scores separately for adverse side effects and therapeutic effects, and then calculate overall scores based on the interpolated scores to generate the single umbrella graphical marking.

Figure 5:
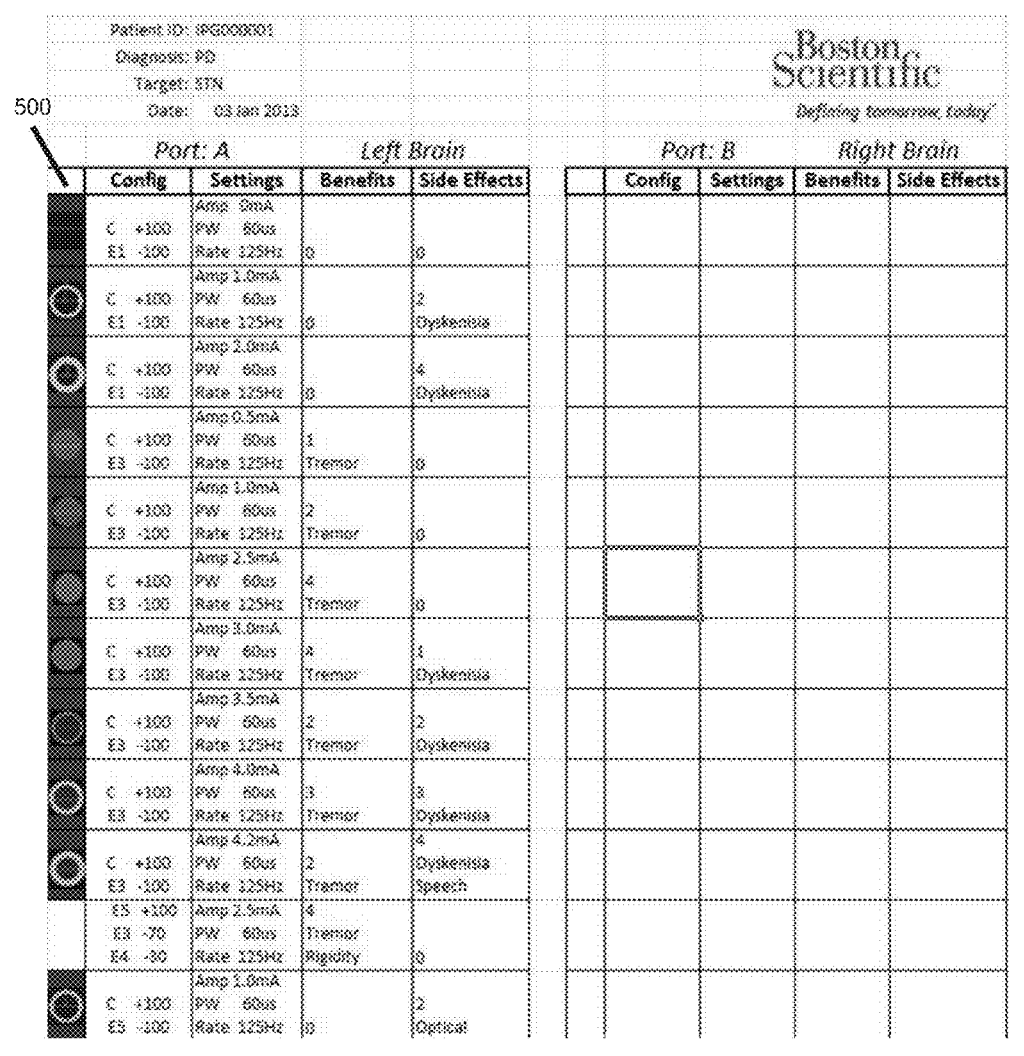

According to an example embodiment of the present invention, the system is configured to generate a report including information of previously implemented stimulation sessions according to user input filter criteria, where, for each particular row, all information used for generating the data of the respective row corresponds to use of the same electrode number (actual or virtual) and amplitude setting. Using the clinical response data of the records that satisfy the filter criteria, the system is configured to generate, for each row for whose electrode number and amplitude value clinical response data is available, a respective graphical marking 108 as described above, and display the generated graphical marking 108 in a cell of the respective row. For example, the system generates the report with a column in which graphical markings 108 are displayed for those rows corresponding to an electrode and amplitude value for which clinical response data is available. For example, FIG. 5 is an example report generated according to an example embodiment of the present invention. Column 1 500 includes graphical markings 108 for all of the populated rows except the second to last row which corresponds to an electrode and amplitude value for which no clinical responds data has been recorded.

Stimulation parameters can be set by a clinician logging into a programming platform under a clinician profile, and can be set by a patient logging into the programming platform under a patient profile. However, a clinician may want to limit the amount of control the patient has over the stimulation settings. For example, the clinician may determine that certain minimum and/or maximum amplitude levels must be met. Accordingly, according to an example embodiment, the system is configured to receive input from a clinician of amplitude limits which the patient cannot violate. According to an example embodiment, the system is configured to visually indicate such a limit(s) in the map 102. For example, in an example embodiment, the system displays a line representing a maximum amplitude level and/or a line representing a minimum amplitude level extending perpendicular to the amplitude axis, and at respective positions along the amplitude axis, the respective positions corresponding to the respective maximum and/or minim amplitude values input by the clinician (or, in an example embodiment, default values if not altered or removed by the clinician). For example, a line displayed at a first amplitude position and a second line displayed a second higher amplitude position would be recognized as corresponding to minimum and maximum values. Alternatively, the lines additionally otherwise graphically or textually indicate whether the line corresponds to a maximum or minimum. Additionally, according to an example embodiment, where only a maximum amplitude or only a minimum amplitude is set, so that only a single limit line is displayed (so that context does not indicate whether the line is a maximum or minimum limit), the line graphically or textually identifies whether the line represents a maximum or minimum limit. For example, text can be printed along the line to textually identify the line, or predefined colors and/or line forms (dashed, dotted, etc.) can be used.

Figure 6:
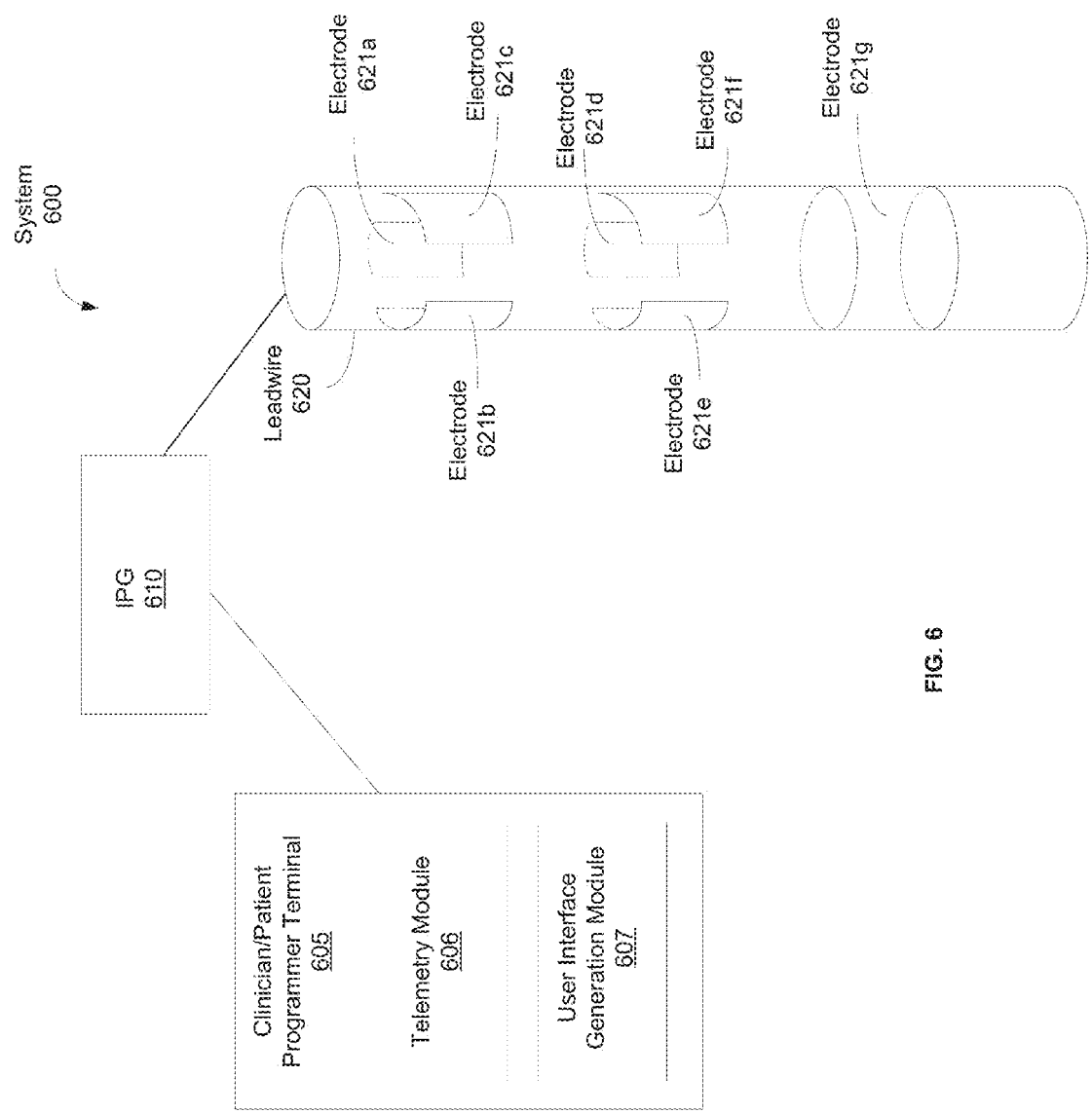
FIG. 6 shows a system according to an example embodiment of the present invention.

FIG. 6 shows an example system according to an example embodiment of the present invention. In an example embodiment, a system 600 includes a clinician and/or patient programmer terminal 605 that includes a telemetry module 606 and a user interface generation module 607. The telemetry module 606 is in communication with an implanted pulse generator (IPG) 610. The user interface generation module 607 includes software executable by a processor for generating graphical user interface displays, as described above, for example, including code for generating the various described graphical markings and soft controls and for recording and displaying clinical effects information. In an example embodiment, interaction with one or more graphical user interface displays and/or a hardware input device is usable for input of one or more stimulation parameter settings in accordance with which the telemetry module 606 outputs instructions to the IPG 610, the IPG 610 accordingly controlling a leadwire 620 to activate one or more electrodes 621*a*-621*g* to produce electric pulses at specified amplitudes. For example, the leadwire 620 is implanted in a patient, e.g., in the patient's brain, and the electric pulses are intended to activate anatomic fibers to produce a therapeutic effect, e.g., as described in further detail in the '330, '312, '340, '343, and '314 applications. The electrodes 621*a*-621*g* can include one or more directional electrodes which can be controlled to direct stimulation in a particular radial direction from the central longitudinal axis of the leadwire 620 and/or can include one or more cylindrical electrodes that produce essentially the same stimulation in all directions rotationally about the cylindrically symmetrical stimulation about the central longitudinal axis of the leadwire 620. As described above, according to an example embodiment, the user interface displays provide for navigation of a clinical effects map to select the parameters for the instructions provided to the IPG 610.

The above description is intended to be illustrative, and not restrictive. Those skilled in the art can appreciate from the foregoing description that the present invention can be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

What is claimed is:

1. A computer-implemented clinical data output method comprising:
   based on at least a subset of stored data of clinical effects, comprising a first clinical effect and a second clinical effect, of one or more stimulations of anatomical tissue performed using electrodes of an implanted leadwire, generating and outputting, by a computer processor, a plurality of graphical markings representing the at least the subset of the stored data by plotting each of the graphical markings at a respective coordinate of a graph, wherein each of the graphical markings represents a respective portion of the at least the subset of the stored data and is output in association with a respective set of values for each of at least two parameters by which one or more the stimulations were performed, wherein each of the graphical markings comprising a center region corresponding to one of a respective clinical effect type of the first clinical effect or a respective score of the first clinical effect and a boundary corresponding to one of a respective clinical effect type of the second clinical effect or a respective score of the second clinical effect; and
   responsive to selection of one of the graphical markings and selection of a programming control indicator, transmitting stimulation parameters to an implantable pulse generator corresponding to the selected one of the graphical markings to produce stimulation of patient tissue using the transmitted stimulation parameters.

2. The method of claim 1, wherein the data of clinical effects is stored at a central cloud database accessible by a plurality of terminals via a network.

3. The method of claim 1, wherein the data of clinical effects is stored on a stimulation device that controls the implanted leadwire.

4. The method of claim 1, wherein the data of clinical effects is stored on the implanted leadwire.

5. The method of claim 1, wherein the data of clinical effects is stored in a local database of a computer terminal of which the computer processor is a part.

6. The method of claim 1, wherein:
   the graph includes a first axis corresponding to values of a first of the at least two parameters and a second axis corresponding to values of a second of the at least two parameters; and
   the association with the respective set of values is via the location at which the respective graphical marking is plotted.

7. The method of claim 6, wherein the first parameter is a leadwire location and the second parameter is a stimulation amplitude.

8. The method of claim 7, wherein the stimulation amplitude is a current amplitude.

9. The method of claim 7, wherein the stimulation amplitude is a voltage amplitude.

10. The method of claim 6, wherein each of the graphical markings is selectable, and the method further comprises:

responsive to a selection of one of the graphical markings, displaying, by the processor, textual details from the stored data of clinical effects on which basis the respective selected graphical marking was generated.

11. The method of claim 10, wherein the selected graphical marking is generated based on data of clinical effects of a plurality of stimulations, and the textual details are based on only one of the plurality of stimulations.

12. The method of claim 11, wherein different ones of the plurality of stimulations occurred at different times, and the method further comprises:
displaying, by the processor, a user-interactive control, user-selection of which is responded to by the processor by replacing the displayed textual details corresponding to a first one of the stimulations with textual details corresponding to a second one of the stimulations that chronologically precedes or follows the first one of the stimulations.

13. The method of claim 6, wherein each of the graphical markings is selectable, and the method further comprises:
displaying, by the processor, a plurality of clinical effect detail indicators, each corresponding to one of a respective clinical effect type or a respective degree of clinical effect; and
responsive to a selection of one of the graphical markings, selectively highlighting, by the processor, those of the clinical effect detail indicators that are associated with the selected graphical marking.

14. The method of claim 13, further comprising:
responsive to user-selection of one of the plurality of clinical effect detail indicators, recording new clinical effects data in association with stimulation parameters to which the selected graphical marking corresponds.

15. The method of claim 14, further comprising:
updating the selected graphical marking in response to the user-selection of the one of the plurality of clinical effect detail indicators.

16. The method of claim 14, wherein, subsequent to the user-selection of the one of the plurality of clinical effect detail indicators and a subsequent navigation away from the selected graphical marking, responsive to a new selection of the graphical marking, the user-selected one of the plurality of clinical effect detail indicators is highlighted based on the prior user-selection of the respective clinical effect detail indicator.

17. The method of claim 13, further comprising:
responsive to user-selection of one of the plurality of clinical effect detail indicators, recording new clinical effects data in association with stimulation parameters of a currently selected stimulation program, and one of updating or generating a graphical marking at one of the coordinates which corresponds to the stimulation parameters of the currently selected stimulation program.

18. The method of claim 6, wherein each of the coordinates of the graph is selectable, and the method further comprises:
responsive to a user-selection of one of the plurality of clinical effect detail indicators and a user-selection of one of the coordinates of the graph:
updating, by the processor, the stored data of clinical effects; and
one of generating or updating, by the processor, a graphical marking for display at the selected one of the coordinates.

19. The method of claim 18, further comprising:
displaying, by the processor, a selectable clinical effect menu control, responsive to selection of which the processor is configured to display a menu of additional selectable clinical effect detail indicators corresponding to clinical effect types other than those to which the plurality of clinical effect detail indicators correspond.

20. The method of claim 19, further comprising:
responsive to a selection of one of the graphical markings for which one of the additional selectable clinical effect indicators had been previously selected, selectively highlighting, by the processor, the clinical effect menu control.

21. The method of claim 6, further comprising:
responsive to user manipulation of a navigation control, shifting focus, by the processor, from a first one of the coordinates of the graph to a second one of the coordinates of the graph, wherein the navigation control includes:
a first navigation component, each selection of which the processor is configured to interpret as an instruction to shift coordinate focus in the graph in a first direction along the first axis;
a second navigation component, each selection of which the processor is configured to interpret as an instruction to shift coordinate focus in the graph in a second direction along the first axis;
a third navigation component, each selection of which the processor is configured to interpret as an instruction to shift coordinate focus in the graph in a first direction along the second axis; and
a fourth navigation component, each selection of which the processor is configured to interpret as an instruction to shift coordinate focus in the graph in a second direction along the second axis.

22. The method of claim 21, further comprising:
responsive to user-manipulation of a step-size control, modifying, by the processor, a step-size setting for each of at least one of the first, second, third, or fourth navigation components, wherein, for a single value of the step-size setting, the coordinate focus shift for each selection of the at least one of the first, second, third, or fourth navigation components is by a same amount, the amount being based on the value of the step-size setting.

23. The method of claim 22, wherein the amount of the coordinate focus shift corresponds to a change in value of the respective parameter to which the respective axis of the respective navigation component corresponds, which change in value is equal to the value of the step-size setting.

24. The method of claim 22, wherein the step-size control is a toggle control for toggling between pre-set toggle-size values.

25. The method of claim 6, further comprising:
displaying, by the processor, a graphical representation of an anatomical structure in which the leadwire is implanted, wherein the graph is displayed within at least a portion of the graphical representation of the anatomical structure.

26. The method of claim 25, further comprising:
determining, by the processor, a relative position of the graph to the graphical representation of the anatomical structure based on a recorded implant location of the leadwire.

27. The method of claim 6, wherein the coordinates of the graph are selectable, the method further comprising:

responsive to selection of one of the coordinates, displaying, by the processor a concentric stimulation magnitude indicator that is centered on the first axis at a value of the first axis corresponding to the selected coordinate and whose outer perimeter one of reaches or crosses the selected coordinate.

28. The method of claim 6, wherein the graph includes a subset of coordinates with which none of the stored data of clinical effects on which basis the graphical markings of the graph are generated is associated, the method further comprising:
interpolating, by the processor, the stored data of clinical effects on which basis the graphical markings of the graph are generated to calculate values for the subset of coordinates; and
displaying, by the processor and in the graph, a graphical screen that gradually varies with respect to a graphical characteristic, the variation in the graphical screen being based on the calculated values obtained by the interpolation.

29. The method of claim 6, further comprising:
displaying, by the processor and one of in the graph, on at least one of the axes, or alongside the at least one of the axes, at least one limit marker, each of the at least one limit marker representing a respective limit to which modification of a value of a respective one of the at least two parameters is permitted.

30. The method of claim 29, further comprising:
obtaining user input of the at least one limit.

31. The method of claim 30, wherein:
the user input of the at least one limit is received in association with a user profile associated with predefined clinician rights; and
in accordance with the obtained user input, an instruction, received in association with a user profile associated with predefined patient rights, to set any of the at least two parameters to a value that is beyond a respective one of the at least one limit that corresponds to the respective parameter, is not followed.

32. The method of claim 6, wherein the coordinates of the graph are selectable, the method further comprising:
programming, by the processor and based on a selection of one of the coordinates of the graph, a stimulation device for operating the implanted leadwire to stimulate anatomical tissue using values of the first and second parameters corresponding to the selected coordinate.

33. The method of claim 32, wherein the coordinates of the graph are selectable by a first type of selection in response to which detailed information corresponding to the selected coordinate are displayed and by a second type of selection in response to which the processor performs the programming of the stimulation device.

34. The method of claim 33, wherein the coordinates of the graph are selectable by a third type of selection in response to which the processor activates a mode by which to enter new clinical effects data.

35. The method of claim 34, wherein the first, second, and third types of selections include a right-click, a left-click, and a touch via touchscreen.

36. The method of claim 6, wherein:
the coordinates of the graph are selectable;
a plurality of leadwires are implanted;
a plurality of stimulation programs are user-definable via a programming module, each of the plurality of stimulation programs defining respective stimulation parameters for each of the plurality of leadwires; and
the method further comprises:
displaying the graph in a user interface screen in which a list of the defined programs is displayed, each of the displayed listings of the defined programs being selectable for toggling between an expanded view in which the plurality of leadwires are listed as child nodes of the selected listing and a collapsed view in which no child nodes of the respective listing are displayed, and each of the displayed listings of the respective leadwires is selectable from within the expanded view of one of the program listings for which the respective leadwire listing is displayed; and
in accordance with a selection of one of the coordinates of the graph, updating settings of the leadwire of a selected one of the leadwire listings for a selected one of the program listings with values of the first and second parameters corresponding to the selected coordinate.

37. The method of claim 1, the method further comprising:
obtaining, by the processor, user input filter criteria, wherein the stored data of clinical effects includes more than the subset set thereof, and, in accordance with the user input filter criteria, the generating of the graphical markings is based selectively on the subset and not the remainder of the stored data of clinical effects.

38. The method of claim 1, wherein the first clinical effect is a therapeutic effect and the second clinical effect is a side effect.

39. The method of claim 1, wherein:
a graphical characteristic of the center region of the graphical markings is set in accordance with a score based on the first clinical effect associated with the set of values with which the respective graphical marking is associated; and
a graphical characteristic of the boundary of the graphical markings is set in accordance with a score calculated based on the second clinical effect associated with the set of values with which the respective graphical marking is associated.

40. The method of claim 1, wherein the center region is displayed in a first color and the boundary is displayed in a second color different than the first color.

41. The method of claim 40, wherein the first and second color vary in transparency based on scores associated with the first and second clinical effects, respectively.

42. The method of claim 41, wherein, for graphical markings where no second clinical effect is present at the corresponding set of values, the boundary is entirely transparent.

* * * * *